United States Patent [19]

Mullin et al.

[11] Patent Number: 5,117,021
[45] Date of Patent: May 26, 1992

[54] METHOD FOR PURIFICATION OF TELLURIUM AND SELENIUM ALKYLS

[75] Inventors: John B. Mullin, West Malvern, England; David J. Cole-Hamilton, Boarhills by St. Andrews, Scotland; Deodatta V. Shenai-Khatkhate, Woburn, Mass.; Paul Webb, Didcot, England

[73] Assignee: The Secretary of State for Defense in Her Britannic Majesty's Government of the United Kingdom of Great Britain and Northern Ireland, London, England

[21] Appl. No.: 536,579
[22] PCT Filed: Dec. 2, 1988
[86] PCT No.: PCT/GB88/01062
 § 371 Date: Jul. 31, 1990
 § 102(e) Date: Jul. 31, 1990
[87] PCT Pub. No.: WO89/05293

PCT Pub. Date: Jun. 15, 1989

[30] Foreign Application Priority Data

Dec. 4, 1987 [GB] United Kingdom ................. 8728392

[51] Int. Cl.$^5$ ....................... C07F 3/08; C07C 391/00
[52] U.S. Cl. ..................... 556/130; 562/899
[58] Field of Search ......................... 556/130; 562/899

[56] References Cited

U.S. PATENT DOCUMENTS 4,946,994 8/1990 Higa ..................................... 562/899

Primary Examiner—Paul F. Shaver
Attorney, Agent, or Firm—Nixon & Vanderhye

[57] ABSTRACT

Tellurium and selenium alkyls are purified by thermal dissociation of the adduct of the compound with a Group IB or IIB metal.

13 Claims, No Drawings

METHOD FOR PURIFICATION OF TELLURIUM AND SELENIUM ALKYLS

This invention relates to methods for the purification of tellurium and selenium alkyls, particularly the dialkyls of these metals.

Tellurium and selenium alkyls are important compounds used in the semiconductor industry, for example in the preparation of cadmium mercury telluride (CMT) used in opto-electronic applications. In many such uses the alkyls are decomposed, usually thermally to form the element, which may itself be deposited on a substrate, or combined with other elements in compounds. It is a very important requirement of such alkyls that they be extremely pure, as the presence of even minute quantities of impurities eg on a ppm level can have a detrimental effect on the properties of the semiconductor.

Present methods of purification of tellurium and selenium alkyls generally involve fractional distillation and are unable to easily reach the abovementioned levels of purity. Another known method of purifying metal alkyls involves the formation of an adduct that has properties which allow it to be decomposed in such a way that the pure alkyl is formed as a decomposition product.

The use of adducts in this way to purify tellurium and selenium alkyls is as yet unknown, although some work has been done to investigate various adducts of these alkyls. For example G E Coates, J Chem Soc (1951) pp 2003-2013, Challenger & North, J Chem Soc (1934) 1 pp 68-71, Carr & Pearson, J Chem Soc (1938) p 282, and Ferguson & Loh, Austral. J Chem (1973) 26 pp 2615-22 all mention that these adducts dissociate with relative ease, but none have been previously known to dissociate in such a way as to yield the pure alkyls.

The present invention seeks to overcome the problems of prior art methods of purification of tellurium and selenium alkyls by novel routes using adducts, some of which are themselves novel.

According to the present invention, there is provided a method of purification of a tellurium or selenium alkyl, which is characterised by forming an adduct of the alkyl with at least one compound of a Group IB or IIB metal (Cu, Ag, Au, Zn, Cd, Hg) and thermally dissociating the said adduct to yield the alkyl. Preferably the at least one compound of a group 11 or 12 metal is an inorganic compound.

The method is suitable for the purification of all tellurium and selenium alkyls, but is particularly suitable for the metal dialkyls. The alkyl group may be straight or branched chain, and is preferably a lower alkyl eg containing up to 4 carbon atoms. These lower alkyls are most useful for semiconductor production.

Preferred Group 11 or 12 metals are cadmium, mercury and copper. The compound is preferably a halide or nitrate, most preferably halides, these being bromides, chlorides and iodides. The most preferred compounds are therefore: CuI, $CdI_2$, $CdBr_2$, $HgCl_2$, $Cu_2I_2$, $HgI_2$.

Preferably the method is carried out in the following way:

(i) A solution of the alkyl in a suitable solvent is prepared, and this is added to a solution of the metal compound in a suitable solvent, preferably an organic solvent.

Preferred solvents in both cases are polar aliphatic organic solvents containing 1 to 10 carbon atoms, preferably 1 to 5. It is desirable to use a solvent for the alkyl that is also capable of dissolving the metal compound.

Suitable solvents for the alkyl include ethers, such as THF but especially diethyl ether; alcohols, especially ethanol; and nitriles especially acetonitrile. These solvents are also suitable for the metal compound.

Typically the alkyl is dissolved in an ether and is added at an appropriate rate to a solution of the metal compound in an alcohol. Preferably the amount of alkyl and metal compound used are in approximately stoichiometric ratios.

(ii) When reaction appears to be complete, excess solvents may be separated by filtration from any precipitated product, or alternately or additionally the bulk of the solvent may be removed by evaporation.

(iii) The solid adduct product is washed with an appropriate solvent, eg the ether used in the reaction, and excess volatiles removed in vacuo.

(iv) The adduct is thermally dissociated in vacuo to yield the pure alkyl which may be collected in a cooled receiver. Suitable dissociation temperatures will depend upon the adduct and are easily determined experimentally. Generally temperatures in the range 80°-150° C. are suitable.

It is preferred that the preparation and subsequent manipulation of the adduct is performed under an inert atmosphere such as nitrogen.

Appropriate conditions for the preparation of any particular tellurium or selenium alkyl can be easily determined experimentally generally following the procedure outlines above. Alkyls purified by the process of the invention are in many instances in a state of purity suitable for their use directly in the preparation of semiconductors, for example the epitaxial deposit of CMT.

The invention will now be described by way of example only.

Table 1 below lists various adducts which were prepared using the method of the two preparative examples and some of their characteristics. Table 2 below lists the microanalytical data for the various adducts.

Certain of the adducts described below are novel, ie:

$((C_2H_5)_2Te)_2CdI_2$ $(C_2H_5)_2Te(CdBr_2)_2$ $((C_2H_5)_2Te)_2CdBr_2$ $((iso-C_3H_7)_2Te)_2CdI_2$ $((iso-C_3H_7)_2Te)_2CdBr_2$ $(iso-C_3H_7)_2Te.CdI_2$

TABLE 1

Adducts for the purification of dialkyltellurium compounds

| Adduct employed | Thermal behaviour (°C.) melts | Thermal behaviour (°C.) dissociates | % Yield of dialkyltellurium |
|---|---|---|---|
| $(Et_2Te)_2.CdI_2$ | ~40 | 90 | 37 |
| $Et_2Te.(CdBr_2)_2$ | — | ≦80 | 67 |
| $Et_2Te.HgCl_2$ | ~100 | ~100-120 | 65 |
| $(Et_2Te.CuI)_n$ | — | ≦120 | 47 |
| $Et_2Te.HgI_2$ | 45 | ≦140 | 50 |
| $^iPr_2Te.CdI_2$ | ~40 | ≦130 | 51 |
| $(^iPr_2Te)_2.CdBr_2$ | — | <125 | 66 |

TABLE 1-continued

Adducts for the purification of dialkyltellurium compounds

| Adduct employed | Thermal behaviour (°C.) melts | Thermal behaviour (°C.) dissociates | % Yield of dialkyltellurium |
|---|---|---|---|
| (iPr₂Te)₂·CdI₂ | — | <125 | 53 | n is variable and the compound maybe polymeric

TABLE 2

Preparation of Adducts of R₂Te with Group 11 & 12 Metal compounds

| Dialkyltellurium (R₂Te) | Metal Compd. MX$_n$ | Solvent Employed* | R₂Te:MX$_n$ ratio in the adduct | Analysis (%) found (theoretical) C | Analysis (%) found (theoretical) H |
|---|---|---|---|---|---|
| Diethyltellurium (C₂H₅)₂Te | CdI₂ | Ethanol | 2:1 | 12.2 (13.0) | 2.5 (2.7) |
| | CdBr₂ | Ethanol | 1:2 | 5.7 (6.5) | 1.1 (1.3) |
| | CdBr₂ | Ethanol | 2:1 | 14.2 (14.9) | 3.1 (2.8) |
| | HgCl₂ | Diethylether | 1:1 | 10.4 (10.5) | 2.2 (2.2) |
| | HgI₂ | Ethanol | 2:1 | 11.9 (11.6) | 2.2 (2.6) |
| | Cu₂I₂ | Acetonitrile | 1:1 | 12.7 (12.7) | 2.6 (2.6) |
| Di-isopropyltellurium [(CH₃)₂CH]₂Te | CdI₂ | Ethanol | 2:1 | 18.4 (18.1) | 3.6 (3.5) |
| | CdBr₂ | Ethanol | 2:1 | 14.7 (14.8) | 2.8 (2.9) |
| ((CH₃)₂CH)₂Te | CdI₂ | Ethanol | 1:1 | 12.4 (12.8) | 2.4 (2.6) |

*In each case, an ethereal solution of R₂Te was added to the metal halide in the solvent shown.

PREPARATIVE EXAMPLE 1

Purification of Diethyltellurium Using Cadmium Iodide

A solution of diethyltellurium (25.5 g, 0.1373 gmol) in diethylether (50 cm³) was added dropwise to a solution of cadmium iodide (24.1 g, 0.065 gmol) in ethanol (350 cm³) to obtain a white precipitate which dissolved on warming to 50° C. The reaction mixture was cooled and stirred at room temperature for 30 minutes. The volume was reduced to ca 100 cm³ in vacuo and the product was obtained as white crystals on cooling to −30° C. overnight. The crystals were isolated from the reaction mixture by filtration under a nitrogen atmosphere and by successive washings with petroleum ether cooled to 4° C. The crystals were pumped to remove any volatile impurities for 1 h at room temperature.

Microanalytical data suggested that the product had a limiting empirical formula (Et₂Te)₂CdI₂.

The pure adduct, (Et₂Te)₂CdI₂ (34.95 g, 0.0473 gmol) was then heated to 100° C. Pure diethyltellurium distilled and was collected in vacuo in a cold trap (11.00 g, 0.0592 gmol, 62.52% yield). The adduct was found to dissociate between 85°–90° C.

PREPARATIVE EXAMPLE 2

Purification of Diethyltellurium Using Copper (I) Iodide

A solution of diethyltellurium (6.6 g, 0.0355 gmol) in diethylether (25 cm³) was added dropwise to a solution of copper (I) iodide (3.5 g, 0.0183 gmol) in acetonitrile (50 cm³). A pale pink microcrystalline precipitate formed during the addition. The excess diethyltellurium and acetonitrile were removed by filtration under a nitrogen atmosphere and by successive washings with petroleum ether cooled to 4° C. The adduct obtained was pumped for 1 h at room temperature to remove any volatile impurities.

Microanalytical studies revealed a limiting empirical formula (Et₂Te)CuI.

The adduct, (Et₂Te)CuI was then heated to 150° C. in vacuo. Pure diethyltellurium distilled and was collected in a cold trap. No sublimation of the adduct was found to occur up to 150° C. The dissociation of the adduct was found to occur between 110°–130° C.

PREPARATIVE EXAMPLE 3

Purification of Di-isopropyltellurium Using Cadmium Iodide

A solution of di-isopropyl tellurium (26.34 g, 0.1253 g mol.) in diethyl ether (150 cm³) was added dropwise to a solution of cadmium iodide (22.50 g, 0.0614 g mol.) in ethanol (200 cm³). The reaction mixture was cooled to −30° C. overnight and the product obtained as white needle crystals. The crystals were isolated from the reaction mixture by filtration under a nitrogen atmosphere and by successive washings with petroleum ether, pre-cooled to 4° C. The crystals were pumped for 1 hour at room temperature to remove any volatile impurities. Overall yield 25.14 g (51.47%). Microanalysis of the crystals suggested that the product had a limiting empirical formula (iPrTe)₂(CdI₂).

The pure adduct (iPrTe)₂(CdI₂), (25.14 g, 0.0316 g mol.) was heated to about 175° C. Pure di-isopropyl tellurium distilled and was collected in vacuo in a cold trap (7.17 g, 0.0335 g mol., 53% yield). The adduct was found to dissociate between 125° C.–135° C.

PREPARATIVE EXAMPLE 4

Purification of Diethyltellurium Using Cadmium Bromide

A solution of diethyltellurium (23.32 g, 0.1256 g mol) in diethylether (150 cm³) was added dropwise to a solution of cadmium bromide (CdBr₂, 4H₂O, 88.62 g, 0.2574 g mol) in ethanol (200 cm³). A yellowish white microcrystalline precipitate formed during the addition, which was found to redissolve on warming the reaction mixture to 50° C. The solution was cooled and stirred at room temperature for 30 minutes. The colume was then reduced to ca 200 cm³ in vacuo and the product was obtained as white crystals on cooling −30° C. overnight. The crystals were isolated from the reaction mixture by filtration under a nitrogen atmosphere and by successive washings with petroleum ether pre-cooled to 4° C. The crystals were pumped for 1 hour at room temperature to remove any volatile impurities. Overall yield was 93.6% (85.92 g).

Microanalysis of the crystals suggested that the product had a limiting empirical formula (Et₂Te)(CdBr₂)₂.

The pure adduct, (Et₂Te)(CdBr)₂, (85.92 g, 0.092 g mol) was heated to 140° C. Pure diethyltellurium distilled and was collected in vacuo in a cold trap (14.66 g, 0.0789 g mol, 85.85% yield). The adduct was found to dissociate between 80°–90° C.

PREPARATIVE EXAMPLE 5

Purification of Diethyltellurium Using Mercury (II) Iodide

A solution of diethyltellurium (4.78 g 0.025 g mol) was added dropwise to a red solution of mercury (II) iodide (6.16 g, 0.013 g mol) in ethanol (250 cm$^3$) to obtain a pale yellow crystalline product. The product was isolated from the reaction mixture by filtration under a nitrogen atmosphere and by successive washings with petroleum ether pre-cooled to 4° C. The crystals were pumped to remove any volatile impurities for 1 hour at room temperature.

Microanalytical data suggested that the product had a limiting emperical formula $(Et_2Te)_2 HgI_2$.

The pure adduct $(EtTe)_2 HgI_2$ (5-90 g, 7.146 m mol) was then heated to 150° C. Pure diethyl tellurium distilled and was collected in vacuo in a cold trap maintained at −196° C. (1.22 g, 6.573 m mol, 46.99% yield). The adduct was found to dissociate between 120°-140° C.

PREPARATIVE EXAMPLE 6

Purification of Diethyltellurium Using Mercury II Chloride

A solution of diethyltellurium (5.71 g, 0.0307 g mol) was added dropwise to a solution of mercury (II) Chloride (7.39 g, 0.272 g mol) in diethyl ether (250 cm$^3$) to obtain a pale yellow crystalline product. The product was isolated from the reaction mixture by filtration under a nitrogen atmosphere and by sicessive washings with petroleum ether precooled to 4° C. The crystals were pumped to remove any votalite impurities for 1 hour at room temperature.

Microanalytical data suggested that the product had a limiting empirical formula $Et_2Te\, HgCl_2$.

The pure adduct $Et_2T_e\, HgCl_2$ (11.65 g, 0.0254 g mol) was then heated to 120° C. Pure diethyltellurium distilled and was collected in vacuo in a cold trap maintained at the liquid nitrogen temperature. The adduct was found to melt at ca 100° C. and dissociate between 100°-120° C.

PREPARATIVE EXAMPLE 7

Purification of Di-isopropyltellurium Using Cadmium Iodide

A solution of di-isopropyltellurium (61.48 g, 0.288 g mol) in diethyl ether (50 cm$^3$) was added dropwise to a solution of cadmium iodide (130.58 g, 0.3565 g mol) in ethanol (ca 250 cm$^3$) to afford a clear orange solution. The reaction mixture was cooled to −30° C. overnight and the product was obtained as white needle shaped crystals. These crystals were isolated from the reaction mixture by filtration under a nitrogen atmosphere, and by successive washings with petroleum ether precooled to 4° C. The crystals were pumped for 1 hour at room temperature to remove any volatile impurities.

Microanalysis of the product suggested that the product had a limiting composition $(i-C_3H_7)_2Te.CdI_2$.

The pure adduct (192.06 g, 0.331 mol) was heated to ca 130° C. Pure di-isopropyltellurium distilled and was collected in vacuo in a cold trap maintained at −196° C. Yield was 31.26 g, 50.81% based on the starting $(i-C_3H_7)_2Te$.

PREPARATIVE EXAMPLE 8

Purification of Di-isopropyltellurium Using Cadmium Bromide

A solution of di-isopropyltellurium (4.62 g, 0.0216 g mol) in ethanol (50 cm$^3$) was added dropwise to a solution of cadmium bromide ($CdBr_2 4H_2O$, 9.91 g) in ethanol (50 cm$^3$). A yellow-white micro-crystalline precipitate formed during the addition. The product was isolated from the reaction mixture by filtration under a nitrogen atmosphere and by successive washings with petroleum ether pre-cooled to 4° C. The crystals were pumped for 1 hour at room temperature to remove any volatile impurities.

Microanalysis of the crystals suggested that the product had a limiting composition $CdBr_2((i-C_3H_7)_2Te)_2$.

The pure adduct (2.5 g) was heated to ca. 125° C. Pure di-isopropyltellurium distilled and was collected in vacuo in a cold trap maintained at −196° C. Yield was 1.00 g, 65.56% based on the weight of the adduct.

We claim:

1. A method of purification of a tellurium or selenium alkyl characterised by forming an adduct of the alkyl with at least one compound of a group IB or IIB metal (Cu, Ag, Au, Zn, Cd, Hg) and thermally dissociating the said adduct to yield the alkyl.
2. A method of purification according to claim 1 wherein the tellurium or selenium alkyl is a dialkyl.
3. A method of purification according to claim 1 wherein each alkyl group in the tellurium or selenium alkyl contains 1 to 4 carbon atoms.
4. A method of purification according to claim 1 wherein the alkyl is a tellurium alkyl.
5. A method according to claim 1 wherein the compound of a group 11 or 12 metal is a halide or nitrate thereof.
6. A method of purification according to claim 5 wherein the metal compound is a chloride, bromide or iodide.
7. A method of purification according to claim 6 wherein the at least one compound of a group 11 or 12 metal is selected from CuI, $CdI_2$, $CdBr_2$, $HgCl_2$ $Cu_2I_2$ and $HgI_2$.
8. A method of purification according to claim 1 wherein the adduct is formed by reaction between the alkyl and the metal compound in an organic solvent.
9. A method according to claim 8 wherein the solvent is selected from ethers, alcohols and nitriles and mixtures thereof.
10. A method of purification according to claim 1 wherein the adduct is dissociated at 80° C.-150° C.
11. A method of purification according to claim 1 wherein diethyl tellurium is purified by forming an adduct with a compound selected from $CdI_2$, $CdBr_2$, $HgCl_2$, $CuI_2$, and $HgI_2$ and then thermally dissociating the adduct and collecting the alkyl.
12. A method of purification according to claim 1 wherein diisopropyl tellurium is purified by forming an adduct with a compound selected from $CdI_2$ and $CdBr_2$ and then thermally dissociating the adduct and collecting the alkyl.
13. An adduct of dialkyl tellurium having a formula selected from following:

$((C_2H_5)_2Te)_2CdI_2$ $(C_2H_5)_2Te(CdBr_2)_2$ $((C_2H_5)_2Te)_2CdBr_2$ $((i-C_3H_7)_2Te)_2CdI_2$ $((i-C_3H_7)_2Te)_2CdBr_2$ $(i-C_3H_7)_2TeCdI_2$

* * * * *